United States Patent [19]

Eilers

[11] Patent Number: 4,790,937

[45] Date of Patent: Dec. 13, 1988

[54] DIAPHRAGM AND CHAMBER DEVICE

[75] Inventor: George J. Eilers, Evergreen, Colo.

[73] Assignee: Cobe Laboratories, Inc., Lakewood, Colo.

[21] Appl. No.: 865,364

[22] Filed: May 20, 1986

[51] Int. Cl.$^4$ .............................................. B01D 13/00
[52] U.S. Cl. .......................... 210/321.71; 210/321.72
[58] Field of Search ............... 417/393; 222/249, 250; 210/321.3, 321.71, 321.72

[56] References Cited

U.S. PATENT DOCUMENTS 4,204,538  5/1980  Cannon ........................... 222/249 X
4,530,759  7/1985  Schal .............................. 210/188 X

FOREIGN PATENT DOCUMENTS 1077943  5/1954  France ................................. 222/249

Primary Examiner—Frank Spear

[57] ABSTRACT

A diaphragm and chamber device including chamber means for defining a chamber having fixed position walls on opposite sides, a diaphragm in the chamber and sealably mounted between the walls to define first and second regions therein on opposite sides of the diaphragm, the diaphragm being movable in the chamber so as to change the volume of the two regions as the diaphragm moves toward either the wall, a magnet carried by the diaphragm and movable therewith, and a magnet position sensor carried by a the wall and sensing the location of the magnet and thus the diaphragm.

11 Claims, 2 Drawing Sheets

DIAPHRAGM AND CHAMBER DEVICE

FIELD OF THE INVENTION

The invention relates to diaphragm and chamber devices, e.g., those used in balancing flow to and from a dialyzer in a dialysate supply machine.

BACKGROUND OF THE INVENTION

One type of balancing chamber used in dialysate supply machines has rigid outer walls and a diaphragm that divides the chamber into two regions so that as one region is being filled with fresh dialysate the other is discharged of an equal amount of spent dialysate as the diaphragm moves toward one of the rigid walls. When all of the spent dialysate has been discharged from the spent dialysate region, the valves at inlets and outlets to the regions are switched, and the spent dialysate side is filled, as the fresh dialysate side discharges, and the diaphragm moves toward the other wall, until all fresh dialysate has been discharged, and so on.

It is desirable to accurately sense when the diaphragm approaches a wall so that the valves to the chamber switch from one mode to the other at the proper time. Schal U.S. Pat. No. 4,530,759, which is hereby incorporated by reference, discloses sensing when a diaphragm has reached a wall by sensing when a pump supplying dialysate to a region is drawing a sharply increasing electrical current. Flowrate sensors, pressure sensors, and contact switches have been suggested as other mechanisms to sense the end of a stroke in similar applications in Papanek et al. U.S. Pat. No. 4,366,061 (col. 9, lines 40–47); Pinkerton U.S. Pat. No. 4,178,240 (col. 3, lines 18–24) and Schal U.S. Pat. No. 4,267,040 (col. 6, lines 29–47).

SUMMARY OF THE INVENTION

It has been discovered that the position of a diaphragm between walls of a chamber can be accurately sensed by providing a magnet that is carried by and movable with the diaphragm and a magnet position sensor that is carried by a side wall of the chamber.

In preferred embodiments, the magnet position sensor provides an output signal the magnitude of which varies as the distance between the magnet and sensor varies; there are valved inlets and outlets to the chamber regions on opposite sides of the diaphragm, and the valves are controlled in response to signals from the magnet position sensor; there are magnet position sensors carried by both walls; and the balance chamber is connected in parallel with an identical balance chamber. Because the diaphragm need not bottom out, long life of the diaphragm is promoted, and there are no large pressure spikes. There also are very repeatable switching points, as there are no contact elements that could perform unrepeatably after wear.

Other advantages and features of the invention will be apparent from the claims and from the following description of the preferred embodiment thereof.

DESCRIPTION OF THE PREFERRED EMBODIMENT

The drawings will be described first.

Drawings

STRUCTURE

Figure 1:
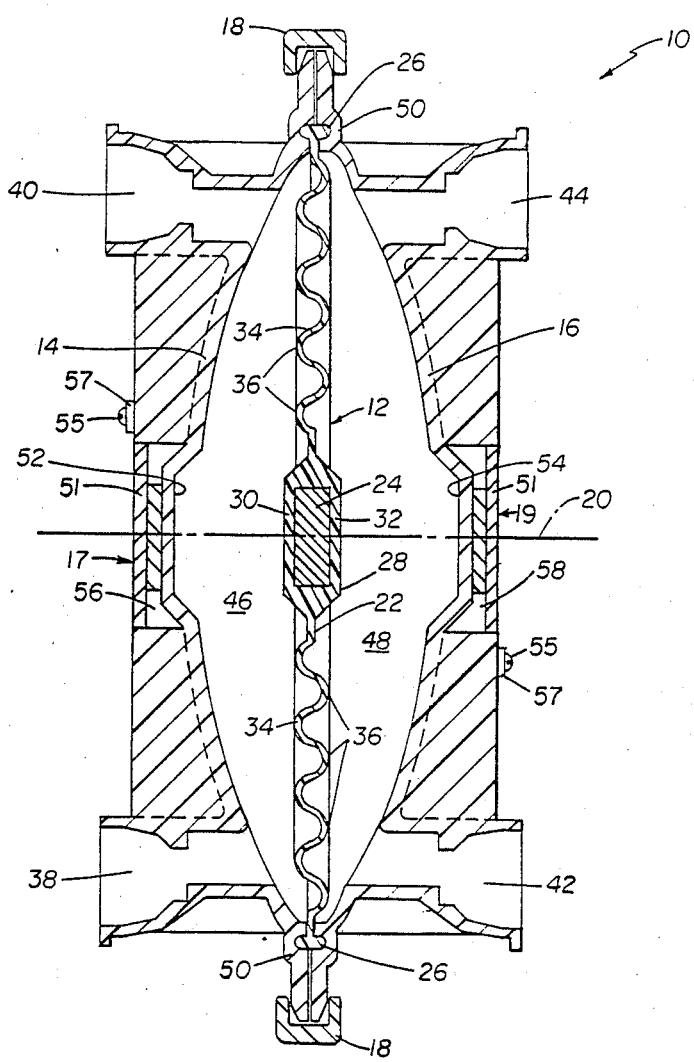
FIG. 1 is a vertical sectional view showing a balance chamber according to the invention.

Referring to FIG. 1, there is shown balance chamber 10 including diaphragm 12, rigid walls 14, 16, peripheral clamp 18, and magnetic position sensors 17, 19.

Diaphragm 12 is symmetrical about horizontal axis 20 and includes generally flat flexible rubber sheet 22 and magnet 24. Sheet 22 is made of ethylene propylene elastomer (available from Bellofram Corp. under the trade designation 270-968) and includes peripheral sealing bead 26 (0.150" in axial direction and 0.060" thick in radial direction), center portion 28, including 0.06±0.02" thick layers 30, 32 on the front and back of magnet 24, and 0.030" thick intermediate corrugated portion 34, including eight annular corrugations 36. The overall thickness of corrugated portion 36 (i.e., the distance along an axis parallel to axis 20) is 0.180"; the dimension of each corrugation along an axis perpendicular to axis 20 is 0.186", and the radius of curvature of each corrugated portion 36 is about 0.105", making the shape of each corrugation 36 in cross-section slightly less than a half circle.

Magnet 24 is 0.49±0.01" in diameter, is 0.19±0.01" thick, and is made of ceramic material (barium or strontium ferrite, Grade 5, oriented and sintered, available from Magnetic Sales and Manufacturing Co., Culver City, Calif.), and molded within flexible sheet 22 in a demagnetized condition (to avoid attracting dirt during manufacture), and magnetized thereafter, having a north pole at one face and a south pole at the other.

Rigid wall 14 has inlet 38 and outlet 40 for fresh dialysate, and rigid wall 16 similarly has inlet 42 and outlet 44 for spent dialysate. Variable volume region 46 between wall 14 and diaphragm 12 is a fresh dialysate region, and variable volume region 48 between diaphragm 12 and wall 16 is a spent dialysate region. Near the peripheries of walls 14, 16 are annular recesses 50 for receiving peripheral sealing bead 26. Rigid walls 14, 16 define recessed regions 52, 54 for receiving center portion 28 of diaphragm 12.

Figure 2:
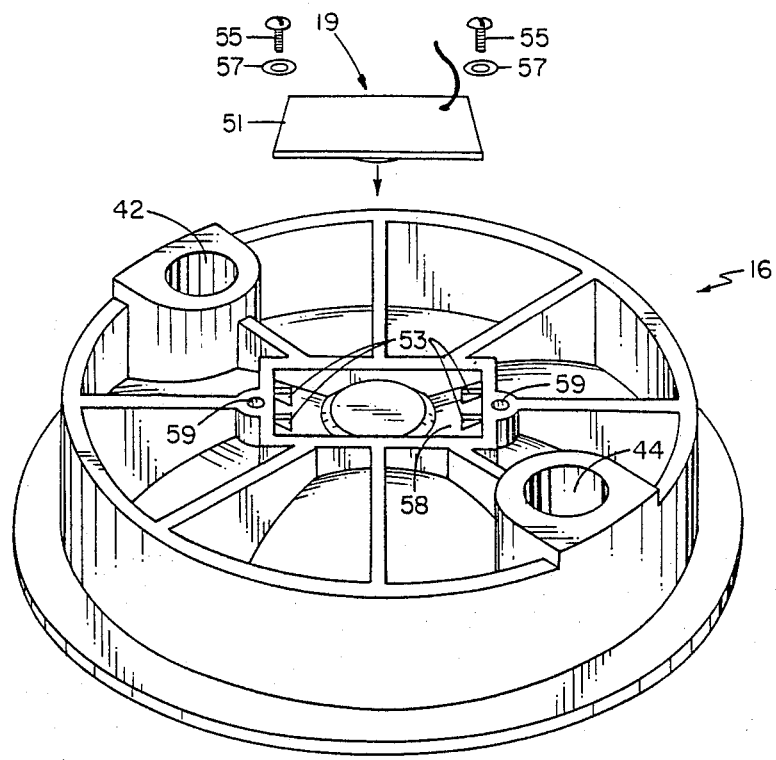
FIG. 2 is a diagrammatic exploded perspective view of part of the FIG. 1 chamber.

Referring to FIGS. 1 and 2, cavities 56, 58, outside and adjacent to recessed regions 52, 54, receive hall effect sensors 17, 19 (FIG. 2), used to sense the position along travel axis 20 of magnet 24. Sensors 17, 19 include circuit boards 51 secured against stops 53 in the ends of recessed regions 52, 54, by overhanging washers 57 and screws 55, which are screwed into screw holes 59. Magnetic position sensors 17, 19 are available from Honeywell, Micro Switch Div., under the trade designation 91SS12-2.

Chamber 10 is connected in parallel with an identical chamber and connected so that one is filling with fresh dialysate and discharging spent dialysate while the other is discharging fresh dialysate and filling with spent dialysate and vice versa.

Figure 3:
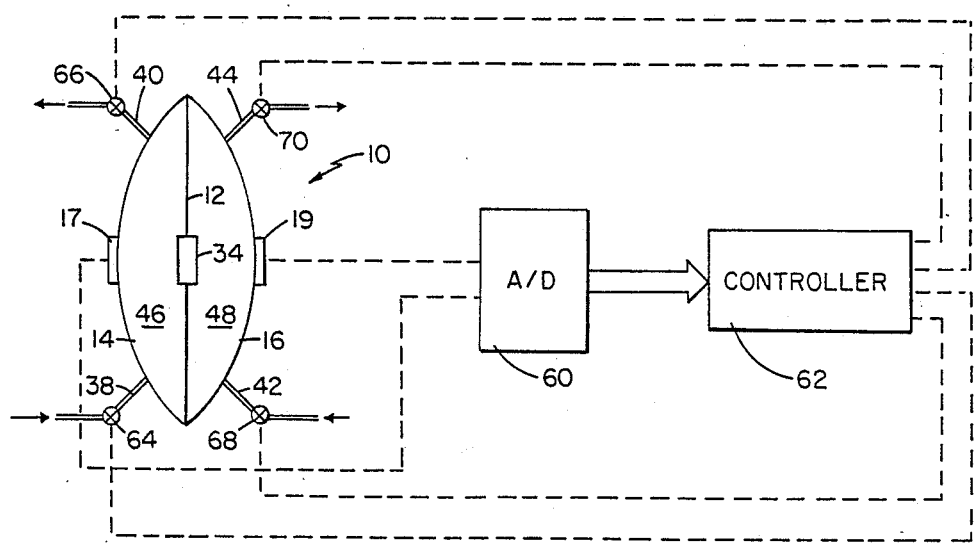
FIG. 3 is a diagram showing the valves and the electronics controlling the FIG. 1 chamber.

Referring to FIG. 3, the electronic control circuitry for chamber 10 is shown. Sensors 17, 19 are connected to analog-to-digital converter 60, in turn connected to electronic controller 62. Controller 62 is connected to provide control signals to two-position (open-closed) solenoid valves 64, 66, 68, 70, controlling flow through fresh dialysate inlet 38, fresh dialysate outlet 40, spent dialysate inlet 42 and spent dialysate outlet 44 respectively.

Operation

Balance chamber 10 is used connected in parallel with an identical balance chamber in a dialysate supply machine. Inlet 38 is connected to a source of fresh dialysate; outlet 40 is connected to a dialyzer; inlet 42 is connected to receive spent dialysate from a dialyzer, and outlet 44 is connected to a drain. Valves to inlets 38, 42 and outlets 40, 44 are controlled so that one balance chamber is receiving, in its region 46, fresh dialysate from a source and discharging spent dialysate from its region 48 to a drain (valves 64, 70 to inlet 38 and outlet 44 being open, valves 66, 68 to outlet 40 and inlet 42 being closed, diaphragm 12 moving to the right) while the other balance chamber is providing fresh dialysate from its region 46 to the dialyzer and receiving spent dialysate in its region 48 from the dialyzer (valves 66, 68 to outlet 40 and inlet 42 being open, valves 64, 70 to inlet 38 and outlet 44 being closed, diaphragm 12 moving to the left).

Travel of diaphragm 12 from one rigid wall to the other is sensed by hall effect sensors 17, 19 in cavities 56, 58. As diaphragm 12 approaches a wall 14 or 16, magnet 24 approaches either sensor 17 or 19 and moves away from the other. Assuming diaphragm 12 is moving to the right (valves 64, 70 open, valves 66, 68 closed), as the magnetic south pole of magnet 24 approaches sensor 19, its output voltage increases as the distance decreases. When microcomputer 62 senses that the output voltage has reached a preset voltage selected so that diaphragm 12 has not bottomed out, it sends control signals to close solenoid valves 64, 70 and open solenoid valves 66, 68 at the same time that the second balance chamber (not shown) is switched the other way. Diaphragm 12 is now moved toward wall 14 by fluid entering inlet 42 and fluid leaving outlet 66. As the magnetic north pole of magnet 24 approaches sensor 17, its output voltage decreases as the distance decreases. When the voltage reaches a preset voltage level, the valves are switched again, and so on.

Balance chamber 10 has long life, as wear on diaphragm 16 is reduced, as it does not bottom out during operation. Also large pressure spikes can be avoided, since one can avoid having the diaphragm bottom out, and the switching points are very repeatable, as the sensors are very accurate and are not subject to wear, as contact switches are. Because of corrugations 36, diaphragm 12 remains symmetrical about axis 20 as it travels along axis 20 in a rolling fashion so that the front and back (north and south) faces of magnet 24 maintain their perpendicular orientation to axis 20, avoiding distortions in the signals of the hall effect sensors sensing magnet position.

Other Embodiments

Other embodiments of the invention are within the scope of the following claims.

What is claimed is:

1. A diaphragm and chamber device comprising
   chamber means for defining a chamber having fixed position walls on opposite sides,
   a diaphragm in said chamber and sealably mounted between said walls to define first and second regions therein on opposite sides of said diaphragm, said diaphragm being movable in said chamber so as to change the volume of said two regions as said diaphragm moves toward either said wall,
   a magnet carried solely by a center portion of said diaphragm and movable therewith, back and forth between said walls completely within said chamber, and
   a magnet position sensor carried by a said wall outside of said chamber and sensing the location of said magnet and thus said diaphragm.

2. The device of claim 1 wherein each said magnet position sensor provides an output signal the magnitude of which varies as the distance between said magnet and said sensor varies.

3. The device of claim 1 wherein said chamber means includes a first inlet and a first outlet to said first region and a second inlet and a second outlet to said second region, and further comprising first and second inlet and outlet valves connected to control flow through said first and second inlets and outlets, respectively, and control means receiving signals from said magnet position sensor and providing valve control signals to said valves.

4. The device of claim 3 wherein said control means provides signals to maintain said first inlet valve and said second outlet valve open while said first outlet valve and second inlet valve are closed and vice versa.

5. The device of claim 1 wherein there is a magnet position sensor carried by each said wall.

6. The device of claim 1 wherein said walls are arcuate.

7. The device of claim 1 wherein said magnet is carried at the center of said diaphragm, and a said wall has a recess for receiving said magnet when said diaphragm is at the end of travel.

8. The device of claim 7 wherein said sensor is mounted on the outside of said wall, adjacent to said wall at a position corresponding to said recess.

9. A dialysate supply machine comprising
   a first fluid flow chamber with a first inlet for connection to source of fresh dialysate, a first outlet for connection to a dialyzer, a second inlet for connection to said dialyzer, a second outlet for connection to a drain,
   valves controlling flow into and out of said inlets and outlets,
   a generally flat flexible sheet within said chamber and dividing said chamber into a fresh dialysate region communicating with said first inlet and outlet and a spent dialysate region communicating with said second inlet and outlet, said generally flat flexible sheet having a periphery sealed to said chamber and a central portion that is reciprocally movable along an axis perpendicular to a plane through said periphery,
   a magnet secured solely to the center of said sheet, said magnet having a front and a rear spaced from each other along said axis, said magnet being movable back and forth between said walls completely within said chamber, and
   a magnet position sensor outside of said chamber and controlling said valves in response to the position of said magnet.

10. The machine of claim 9 further comprising a second fluid flow chamber connected in parallel with the first chamber and controlled to pump fresh dialysate and receive spent dialysate while the first chamber is receiving fresh dialysate and pumping spent dialysate and vice versa.

11. The machine of claim 9 wherein each said magnet position sensor provides an output signal the magnitude of which varies as the distance between said magnet and said sensor varies.

* * * * *